(12) United States Patent
Yanagisawa et al.

(10) Patent No.: US 7,683,184 B2
(45) Date of Patent: Mar. 23, 2010

(54) HETEROCYCLIC COMPOUNDS AND OPTICAL RECORDING MATERIALS

(75) Inventors: Satoshi Yanagisawa, Tokyo (JP); Yusuke Kubota, Tokyo (JP)

(73) Assignee: Adeka Corporation, Tokyo (JP)

( * ) Notice: Subject to any disclaimer, the term of this patent is extended or adjusted under 35 U.S.C. 154(b) by 402 days.

(21) Appl. No.: 11/661,116

(22) PCT Filed: Aug. 18, 2005

(86) PCT No.: PCT/JP2005/015054

§ 371 (c)(1),
(2), (4) Date: Feb. 26, 2007

(87) PCT Pub. No.: WO2006/035554

PCT Pub. Date: Apr. 6, 2006

(65) Prior Publication Data

US 2007/0255058 A1 Nov. 1, 2007

(30) Foreign Application Priority Data

Sep. 27, 2004 (JP) .............................. 2004-279314

(51) Int. Cl.
C07D 209/14 (2006.01)
C07D 211/26 (2006.01)
C07D 265/30 (2006.01)
G11B 7/249 (2006.01)
G11B 7/24 (2006.01)

(52) U.S. Cl. ........................ 548/561; 720/718; 544/143; 546/198; 556/143

(58) Field of Classification Search ................ 548/490, 548/491, 504; 556/144, 145
See application file for complete search history.

(56) References Cited

U.S. PATENT DOCUMENTS

| 5,484,927 A | 1/1996 | Smothers | |
|---|---|---|---|
| 2002/0006494 A1 | 1/2002 | Saito et al. | |
| 2003/0224293 A1* | 12/2003 | Oya et al. | 430/270.14 |

FOREIGN PATENT DOCUMENTS

| JP | 58-157862 | | 9/1983 |
|---|---|---|---|
| JP | 3-11324 | | 1/1991 |
| JP | 7-505911 | | 6/1995 |
| JP | 2001-47740 | | 2/2001 |
| JP | 2001-301333 | | 10/2001 |
| JP | 2002-229195 | | 8/2002 |
| JP | 2002229195 A | * | 8/2002 |
| JP | 2003-171571 | | 6/2003 |
| JP | 2003171571 A | * | 6/2003 |
| JP | 2003-237233 | | 8/2003 |
| WO | WO 01/44374 | | 6/2001 |

* cited by examiner

*Primary Examiner*—Rebecca L Anderson
*Assistant Examiner*—Matthew P Coughlin
(74) *Attorney, Agent, or Firm*—Young & Thompson

(57) ABSTRACT

The heterocyclic compound of the present invention is represented by general formula (I) and is suitable to forming an optical recording layer in an optical recording medium to which short-wavelength light is applied for recording and playing-back.

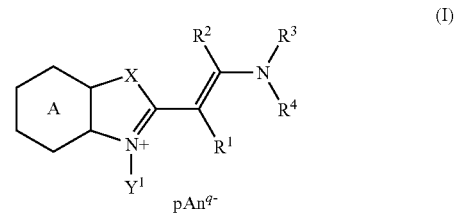

(In the formula, ring A represents a benzene or naphthalene ring optionally substituted with an alkyl, haloalkyl, alkoxy, haloalkoxy or amido group having 1 to 8 carbon atoms, a halogen atom, a cyano group, a nitro group, a sulfonyl or sulfinyl group containing a hydrocarbon group having 1 to 12 carbon atoms, or an alkylamino or dialkylamino group wherein each alkyl has 1 to 8 carbon atoms; X represents $CR^aR^b$, NY, O, S, or Se atom, wherein $R^a$ and $R^b$ each represent a hydrocarbon group having 1 to 12 carbon atoms, which may be united to form a 3- to 6-membered ring, and Y represents a hydrogen atom or an organic group having 1 to 30 carbon atoms; $R^1$ and $R^2$ each represent independently a hydrogen atom, a halogen atom, a cyano group, an alkyl group having 1 to 4 carbon atoms, or an aralkyl group having 7 to 18 carbon atoms; $R^3$ and $R^4$ each represent independently a hydrocarbon group having 1 to 4 carbon atoms or are united to form a heterocycle free from multiple bonds; $Y^1$ represents a hydrogen atom, an organic group having 1 to 30 carbon atoms, or a group represented by general formula (II); $An^{q-}$ represents a q-valent anion; q represents 1 or 2; and p represents a coefficient for satisfying the electric charge neutrality.)

6 Claims, No Drawings

HETEROCYCLIC COMPOUNDS AND OPTICAL RECORDING MATERIALS

TECHNICAL FIELD

The present invention relates to a novel heterocyclic compound and an optical recording material comprising the heterocyclic compound. The heterocyclic compound is not only suitable for an optical recording material but also valuable as a light absorber, a photosensitizer, a UV absorber, and the like.

BACKGROUND ART

Generally, optical recording media have been widely used because of their excellent properties such as high recording capacity, capability of non-contact recording and playing-back, and the like. In rewritable optical discs such as WORM, CD-R, DVD-R, and the like, laser beam is collimated onto a quite small area in an optical recording layer to perform recording through changing the properties of the optical recording layer at the area, and playing-back is performed based on the difference between the amount of light reflected in the recorded area and that in an unrecorded area.

Currently, in the above-mentioned optical disc, the wavelength of semiconductor laser used for recording and playing-back is 750 to 830 nm for CD-R, or 620 to 690 nm for DVD-R. However, for further increasing the capacity, there is examined an optical disc to which a laser having a shorter wavelength is applied; for example an optical disc to which light in 380 to 420 nm is applied for recording.

For an optical recording layer in such an optical recording medium for short-wavelength light, an indole derivative has been examined as an optical recording material. As the indole derivative, for example, Patent Document 1 reported a monomethinecyanine compound, and Patent Document 2 reported an indole compound.

For the optical recording material, the wavelength of the absorption maximum ($\lambda_{max}$) is required to be suitable for the light for recording and the light for playing-back. Furthermore, an optical recording material having a high absorbance is advantageous in terms of recording sensitivity and recording speed. The above-mentioned compounds did not necessarily have characteristics of the absorption wavelength suitable for short-wavelength lasers.

Patent Document 1: Japanese Patent Laid-Open Publication No. 2003-237233

Patent Document 2: WO 01/44374 Pamphlet

DISCLOSURE OF THE INVENTION

Problems to be Solved by the Invention

Accordingly, an object of the present invention is to provide a compound suitable for an optical recording medium to which short-wavelength light is applied for recording and playing-back, and an optical recording material comprising the compound.

Means for Solving the Problems

The present inventors pursued intensive study, and found that a heterocyclic compound having a specific structure is suitable for an optical recording material used in an optical recording layer of an optical recording medium to which laser light in 380 to 420 nm is applied, and accomplished the present invention Namely, the present invention provides a heterocyclic compound represented by general formula (I) below, and an optical recording material that comprises the heterocyclic compound and is used for an optical recording layer in an optical recording medium in which the optical recording layer is formed on a substrate.

[Chemical Formula 1]

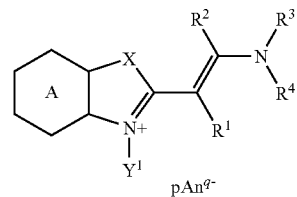

(I)

(In the formula, ring A represents a benzene ring optionally substituted with an alkyl group having 1 to 8 carbon atoms, a haloalkyl group having 1 to 8 carbon atoms, an alkoxy group having 1 to 8 carbon atoms, a haloalkoxy group having 1 to 8 carbon atoms, a cyano group, a nitro group, a sulfonyl group containing a hydrocarbon group having 1 to 12 carbon atoms, a sulfinyl group containing a hydrocarbon group having 1 to 12 carbon atoms, an alkylamino group wherein the alkyl has 1 to 8 carbon atoms, a dialkylamino group wherein each alkyl has 1 to 8 carbon atoms, an amido group having 1 to 8 carbon atoms, or a halogen atom; or a naphthalene ring optionally substituted with an alkyl group having 1 to 8 carbon atoms, a haloalkyl group having 1 to 8 carbon atoms, an alkoxy group having 1 to 8 carbon atoms, a haloalkoxy group having 1 to 8 carbon atoms, a cyano group, a nitro group, a sulfonyl group containing a hydrocarbon group having 1 to 12 carbon atoms, a sulfinyl group containing a hydrocarbon group having 1 to 12 carbon atoms, an alkylamino group wherein the alkyl has 1 to 8 carbon atoms, a dialkylamino group wherein each alkyl has 1 to 8 carbon atoms, an amido group having 1 to 8 carbon atoms, or a halogen atom. X represents $CR^aR^b$, NY, O, S, or Se atom, wherein $R^a$ and $R^b$ each represent a hydrocarbon group having 1 to 12 carbon atoms, which may be united to form a 3- to 6-membered ring, and Y represents a hydrogen atom or an organic group having 1 to 30 carbon atoms. $R^1$ and $R^2$ each represent independently a hydrogen atom, a halogen atom, a cyano group, an alkyl group having 1 to 4 carbon atoms, or an aralkyl group having 7 to 18 carbon atoms. $R^3$ and $R^4$ each represent independently a hydrocarbon group having 1 to 4 carbon atoms or are united to form a heterocycle free from multiple bonds. $Y^1$ represents a hydrogen atom, an organic group having 1 to 30 carbon atoms, or a group represented by general formula (II) below. $An^{q-}$ represents a q-valent anion, q represents 1 or 2, and p represents a coefficient for satisfying the electric charge neutrality.

[Chemical Formula 2]

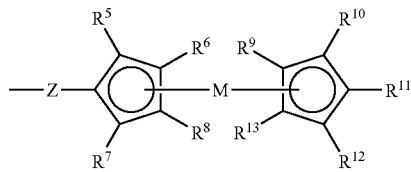

(II)

(In the formula, $R^5$ to $R^{13}$ each represent independently a hydrogen atom, an optionally halogenated alkyl group having 1 to 4 carbon atoms in which (a) methylene group(s) in the chain may be replaced by —O— or —CO—. M represents Fe, Co, Ni, Ti, Cu, Zn, Zr, Cr, Mo, Os, Mn, Ru, Sn, Pd, Rh, or Pt. Z represents a direct bond or an alkylene group having 1 to 8 carbon atoms in which (a) methylene group(s) may be replaced by —O—, —S—, —CO—, —COO—, —OCO—, —SO$_2$—, —NH—, —CONH—, —NHCO—, —N=CH—, or —CH=CH—.)

BEST MODE FOR CARRYING OUT THE INVENTION

As the alkyl group having 1 to 8 carbon atoms serving as the substituent in the benzene ring or naphthalene ring represented by A in general formula (I), there may be mentioned methyl, ethyl, propyl, isopropyl, butyl, sec-butyl, tert-butyl, isobutyl, amyl, isoamyl, tert-amyl, hexyl, cyclohexyl, cyclohexylmethyl, cyclohexylethyl, heptyl, isoheptyl, tert-heptyl, n-octyl, isooctyl, tert-octyl, 2-ethylhexyl, and the like. As the haloalkyl group having 1 to 8 carbon atoms serving as the above substituent, there may be mentioned chloromethyl, dichloromethyl, trichloromethyl, bromomethyl, dibromomethyl, tribromomethyl, fluoromethyl, difluoromethyl, trifluoromethyl, 2,2,2-trifluoroethyl, perfluoroethyl, perfluoropropyl, perfluorobutyl, and the like. The alkoxy group having 1 to 8 carbon atoms that serves as the above substituent includes methoxy, ethoxy, propoxy, isopropoxy, butoxy, sec-butoxy, tert-butoxy, hexyloxy, octyloxy, and the like. The haloalkoxy group having 1 to 8 carbon atoms that serves as the above substituent includes chloromethyloxy, dichloromethyloxy, trichloromethyloxy, bromomethyloxy, dibromomethyloxy, tribromomethyloxy, fluoromethyloxy, difluoromethyloxy, trifluoromethyloxy, 2,2,2-trifluoroethyloxy, perfluoroethyloxy, perfluoropropyloxy, perfluorobutyloxy, and the like. As the hydrocarbon group having 1 to 12 carbon atoms in the sulfonyl or sulfinyl group serving as the above substituent, there may be mentioned an alkyl group such as methyl, ethyl, propyl, isopropyl, butyl, sec-butyl, tert-butyl, isobutyl, amyl, isoamyl, tert-amyl, hexyl, cyclohexyl, cyclohexylmethyl, 2-cyclohexylethyl, heptyl, isoheptyl, tert-heptyl, n-octyl, isooctyl, tert-octyl, 2-ethylhexyl, nonyl, isononyl, decyl, and dodecyl; an alkenyl group such as vinyl, 1-methylethen-1-yl, propen-1-yl, propen-2-yl, propen-3-yl, buten-1-yl, buten-2-yl, 2-methylpropen-3-yl, 1,1-dimethylethen-2-yl, and 1,1-dimethylpropen-3-yl; and an aryl group such as phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, and 2,4,5-trimethylphenyl; and an aralkyl group such as benzyl, 2-methylbenzyl, 3-methylbenzyl, 4-methylbenzyl, 2,4-dimethylbenzyl, phenethyl, 2-phenylpropan-2-yl, diphenylmethyl, styryl, and cinnamyl. As the alkyl group having 1 to 8 carbon atoms in the alkylamino group or dialkylamino group serving as the above substituent, there may be mentioned the alkyl groups having 1 to 8 carbon atoms listed above. As the acyl group composing the amido group having 1 to 8 carbon atoms serving as the substituent, there may be mentioned acetyl, propionyl, octanoyl, acryloyl, methacryloyl, benzoyl, and the like. The halogen atom serving as the substituent includes fluorine, chlorine, bromine, and iodine.

In general formula (I), the hydrocarbon group having 1 to 12 carbon atoms represented by $R^a$ or $R^b$ includes the hydrocarbon group having 1 to 12 carbon atoms listed as that may compose the above sulfonyl group; the 3- to 6-membered ring formed by $R^a$ and $R^b$ that bond to each other includes cyclopropane-1,1-diyl, cyclobutane-1,1-diyl, 2,4-dimethylcyclobutane-1,1-diyl, 3-dimethylcyclobutane-1,1-diyl, cyclopentane-1,1-diyl, and cyclohexane-1,1-diyl. The organic group having 1 to 30 carbon atoms represented by Y is exemplified by, but not limited to, an alkyl group such as methyl, ethyl, propyl, isopropyl, butyl, sec-butyl, tert-butyl, isobutyl, amyl, isoamyl, tert-amyl, hexyl, cyclohexyl, cyclohexylmethyl, 2-cyclohexylethyl, heptyl, isoheptyl, tert-heptyl, n-octyl, isooctyl, tert-octyl, 2-ethylhexyl, nonyl, isononyl, decyl, dodecyl, tridecyl, tetradecyl, pentadecyl, hexadecyl, heptadecyl, and octadecyl; an alkenyl group such as vinyl, 1-methylethenyl, 2-methylethenyl, propenyl, butenyl, isobutenyl, pentenyl, hexenyl, heptenyl, octenyl, decenyl, pentadecenyl, and 1-phenylpropen-3-yl; an alkylaryl group such as phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl) phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, and cyclohexylphenyl; an aralkyl group such as benzyl, phenethyl, 2-phenylpropan-2-yl, diphenylmethyl, triphenylmethyl, styryl, and cinnamyl; and a group in which these hydrocarbon group just listed is interrupted by (an) ether bond(s) and/or (a) thioether bond(s), for example, 2-methoxyethyl, 3-methoxypropyl, 4-methoxybutyl, 2-butoxyethyl, methoxyethoxyethyl, methoxyethoxyethoxyethyl, 3-methoxybutyl, 2-phenoxyethyl, 2-methylthioethyl, and 2-phenylthioethyl. Furthermore, these groups may be substituted with an alkoxy group, an alkenyl group, a nitro group, a cyano group, a halogen atom, or the like.

In general formula (I), the alkyl group having 1 to 4 carbon atoms represented by $R^1$ or $R^2$ includes methyl, ethyl, propyl, isopropyl, butyl, sec-butyl, tert-butyl, and isobutyl; and the aralkyl group having 7 to 18 carbon atoms represented by $R^1$ or $R^2$ includes benzyl, phenethyl, 2-phenylpropan-2-yl, styryl, cinnamyl, diphenylmethyl, triphenylmethyl, and the like. The alkyl group having 1 to 4 carbon atoms represented by $R^3$ or $R^4$ includes the groups listed for $R^1$ or $R^2$, and the heterocycle free from multiple bonds formed by $R^3$ and $R^4$ that bond to each other includes a pyrrolidine ring, an imidazolidine ring, a pyrazolidine ring, a thiazolidine ring, an isothiazolidine ring, an oxazolidine ring, an isooxazolidine ring a piperidine ring, a piperazine ring, a morpholine ring, and the like.

In general formula (I), the organic group having 1 to 30 carbon atoms represented by $Y^1$ includes the groups listed above for Y.

In general formula (I), the anion represented by $An^{q-}$ includes, for example, as a monovalent anion, halide such as chloride, bromide, iodide, and fluoride; an inorganic anion such as perchlorate, chlorate, thiocyanate, hexafluorophosphate, hexafluoroantimonate, and tetrafluoroborate; an organic sulfonate such as benzenesulfonate, toluenesulfonate, trifluoromethanesulfonate, diphenylamine-4-sulfonate, 2-amino-4-methyl-5-chlorobenzenesulfonate, and 2-amino-5-nitrobenzenesulfonate; an organophosphate such as octylphosphate, dodecylphosphate, octadecylphosphate, phenylphosphate, nonylphenylphosphate, and 2,2'-methylenebis(4,6-di-tert-butylphenyl)phosphonate; and the like, and as a divalent anion, benzenedisulfonate, naphthalenedisulfonate, and the like. Furthermore, there may be used, if necessary, a quencher anion, which has function of quenching an activated molecule in the excited state; a metallocene-containing anion having (an) anionic group(s) such as carboxylate, phosphonate, and sulfonate in the cyclopentadienyl ring(s), such as ferrocene or ruthenocene; or the like.

The above quencher anion includes, for example, anions represented by general formula (A) or (B) below, anions described in Japanese Patent Laid-Open Publication Nos. S60-234892, H5-43814, H6-239028, H9-309886, and H10-45767, and the like.

[Chemical Formula 3]

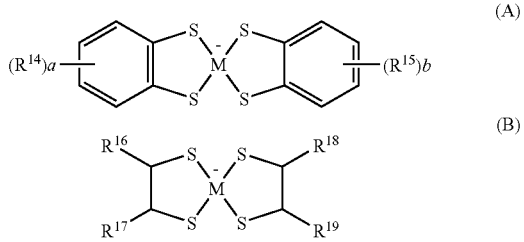

(In the formulae, M represents a nickel atom or a copper atom, $R^{14}$ and $R^{15}$ each represent independently a halogen atom, an alkyl group having 1 to 8 carbon atoms, an aryl group having 6 to 30 carbon atoms, or —SO$_2$-G group, wherein G represents an alkyl group, an optionally halogenated aryl group, a dialkylamino group, a diarylamino group, a piperidino group, or a morpholino group; a and b each represent an integer of 0 to 4. $R^{16}$, $R^{17}$, $R^{18}$, and $R^{19}$ each represent independently an alkyl group, an alkylphenyl group, an alkoxyphenyl group, or a halogenated phenyl group.)

In general formula (II) representing $Y^1$ in general formula (I), the alkyl group having 1 to 4 carbon atoms represented by $R^5$ to $R^{13}$ includes methyl, ethyl, propyl, isopropyl, butyl, sec-butyl, tert-butyl, and isobutyl. The halogenated derivatives of these alkyl groups include chloromethyl, dichloromethyl, trichlorolmethyl, bromomethyl, dibromomethyl, tribromomethyl, fluoromethyl, difluoromethyl, trifluoromethyl, 2,2,2-trifluoroethyl, perfluoroethyl, perfluoropropyl, perfluorobutyl, and the like. As the (halo)alkyl group having 1 to 4 carbon atoms in which (a) methylene group(s) in the chain is(are) replaced by —O—, there may be mentioned methoxy, ethoxy, propoxy, isopropoxy, butoxy, sec-butoxy, tert-butoxy, 2-methoxyethoxy, 2-methoxyethyl, chloromethyloxy, dichloromethyloxy, trichloromethyloxy, bromomethyloxy, dibromomethyloxy, tribromomethyloxy, fluoromethyloxy, difluoromethyloxy, trifluoromethyloxy, 2,2,2-trifluoroethyloxy, perfluoroethyloxy, perfluoropropyloxy, perfluorobutyloxy, and the like. As the group in which a methylene group in the chain of the above (halo)alkyl group having 1 to 4 carbon atoms is replaced by —CO—, there may be mentioned acetyl, propionyl, monochloroacetyl, dichloroacetyl, trichloroacetyl, trifluoroacetyl, propan-2-on-1-yl, butan-2-on-1-yl, and the like.

In general formula (II), the alkylene group having 1 to 8 carbon atoms represented by Z includes methylene, ethylene, propylene, methylethylene, butylene, 1-methylpropylene, 2-methylpropylene, 1,2-dimethylpropylene, 1,3-dimethylpropylene, 1-methylbutylene, 2-methylbutylene, 3-methylbutylene, 4-methylbutylene, 2,4-dimethylbutylene, 1,3-dimethylbutylene, pentylene, hexylene, heptylene, octylene, ethane-1,1-diyl, propane-2,2-diyl, cyclopropane-1,1-diyl, cyclopropane-1,2-diyl, cyclobutane-1,1-diyl, cyclobutane-1,2-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, cyclohexane-1,4-diyl, methylcyclohexane-1,4-diyl, and the like. For the related group in which a methylene group in the chain of such an alkylene group is replaced by —O—, —S—, —CO—, —COO—, —OCO—, —SO$_2$—, —NH—, —CONH—, —NHCO—, —N=CH—, or —CH=CH—, the position and number of the replacement may be arbitrarily selected.

Among the heterocyclic compounds represented by general formula (I), the compound represented by general formula (I') below is preferred because the cost for production is low and has optical properties particularly suitable to an optical recording material used for an optical recording layer in an optical recording medium to which laser light at 380 to 420 nm is applied.

[Chemical Formula 4]

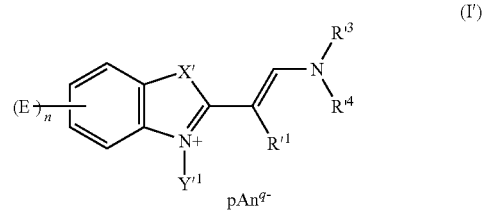

(In the formula, E represents an alkyl group having 1 to 8 carbon atoms, a haloalkyl group having 1 to 8 carbon atoms, an alkoxy group having 1 to 8 carbon atoms, a haloalkoxy group having 1 to 8 carbon atoms, a cyano group, a nitro group, a sulfonyl group containing a hydrocarbon group having 1 to 12 carbon atoms, a sulfinyl group containing a hydrocarbon group having 1 to 12 carbon atoms, an alkylamino group wherein the alkyl has 1 to 8 carbon atoms, a dialkylamino group wherein each alkyl has 1 to 8 carbon atoms, an amido group having 1 to 8 carbon atoms, or a halogen atom. X' represents CR'$^a$R'$^b$, O, or S, wherein R'$^a$ and R'$^b$ each represent a hydrocarbon group having 1 to 12 carbon atoms, which may be united to form a 3- to 6-membered ring. R'$^1$ represents a hydrogen atom, a halogen atom, a cyano group, an alkyl group having 1 to 4 carbon atoms, or an aralkyl group having 7 to 18 carbon atoms. R'$^3$ and R'$^4$ each represent independently a hydrocarbon group having 1 to 4 carbon atoms or are united to form a heterocycle free from multiple bonds. Y'$^1$ represents a hydrogen atom, an organic group having 1 to 30 carbon atoms, or a group represented by general formula (II') below. n represents an integer of 0 to 4. An$^{q-}$, and p are the same as those in general formula (I).)

[Chemical Formula 5]

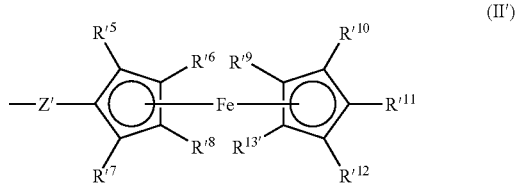

(In the formula, R'$^5$ to R'$^{13}$ each represent independently a hydrogen atom or an optionally halogenated alkyl group having 1 to 4 carbon atoms in which (a) methylene group(s) in the chain is(are) optionally replaced by —O— or —CO—. Z' represents a direct bond or an alkylene group having 1 to 8 carbon atoms.)

In general formula (I'), as the alkyl group having 1 to 8 carbon atoms, the haloalkyl group having 1 to 8 carbon atoms, the alkoxy group having 1 to 8 carbon atoms, the haloalkoxy group having 1 to 8 carbon atoms, a cyano group, a nitro group, the sulfonyl group containing a hydrocarbon group having 1 to 12 carbon atoms, the sulfinyl group containing a hydrocarbon group having 1 to 12 carbon atoms, the alkylamino group wherein the alkyl has 1 to 8 carbon atoms, the dialkylamino group wherein each alkyl has 1 to 8 carbon atoms, and the amido group having 1 to 8 carbon atoms represented by E, there may be mentioned the groups listed as the substituents in A in general formula (I). As the hydrocarbon groups represented by $R^{r a}$ and $R^{r b}$ that have 1 to 12 carbon atoms and are optionally united to form a 3- to 6-membered ring, there may be mentioned the groups listed for $R^a$ and $R^b$ in general formula (I). As the alkyl group having 1 to 4 carbon atoms and the aralkyl group having 7 to 18 carbon atoms represented by $R^{r1}$, there may be mentioned the groups listed for $R^1$ in general formula (I). As the hydrocarbon groups represented by $R^{r3}$ and $R^{r4}$ that have 1 to 4 carbon atoms or the groups that are united to form a heterocycle, there may be mentioned the groups listed for $R^3$ and $R^4$ in general formula (I). As the organic group having 1 to 30 carbon atoms represented by $Y^{r1}$, there may be mentioned the groups listed for Y in general formula (I). When $Y^{r1}$ is the organic group having 1 to 30 carbon atoms, it is preferred that $Y^{r1}$ group is easily introduced and does not substantially affect the optical properties and that the cost for producing the heterocyclic compound is low. Such $Y^{r1}$ includes a hydrocarbon group having 1 to 12 carbon atoms optionally interrupted by (an) oxygen atom(s).

In general formula (II'), as the hydrogen atom, or the optionally halogenated alkyl group having 1 to 4 carbon atoms in which a methylene group in the chain is optionally replaced by —O— or —CO—, there may be mentioned the groups represented as examples of $R^5$ to $R^{13}$ in general formula (II); and as the alkylene group having 1 to 8 carbon atoms represented by Z', there may be mentioned methylene, ethylene, propylene, methylethylene, butylene, 1-methylpropylene, 2-methylpropylene, ethane-1,1-diyl, propane-2,2-diyl, pentylene, hexylene, heptylene, octylene, and the like.

Among the heterocyclic compounds represented by general formula (I'), a heterocyclic compound in which $Y^{r1}$ is the group represented by general formula (II') is particularly excellent in light fastness and particularly suitable for an optical recording material.

Specific preferred example of the heterocyclic compound of the present invention includes compounds No. 1 to No. 66 below. In each formula below, only the cyanine cation is shown, any anion being omitted.

[Chemical Formula 6]

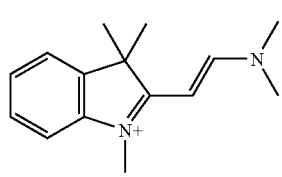

Compound No. 1

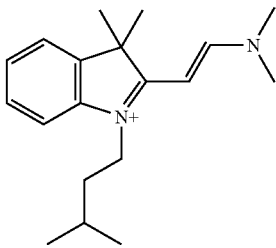

Compound No. 2

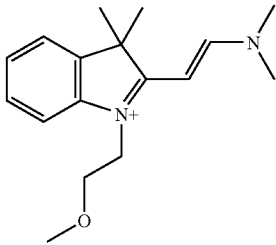

Compound No. 3

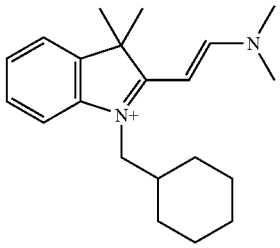

Compound No. 4

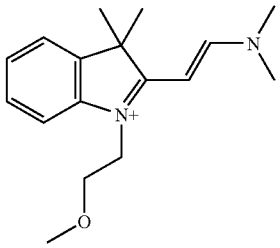

Compound No. 5

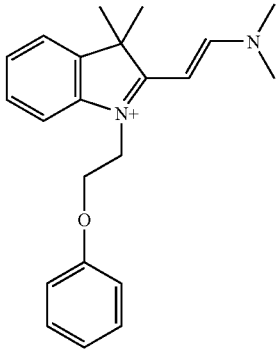

Compound No. 6

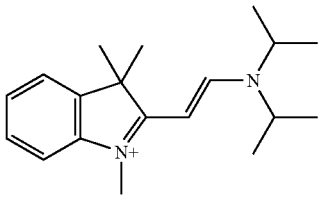

Compound No. 7

-continued
Compound No. 8
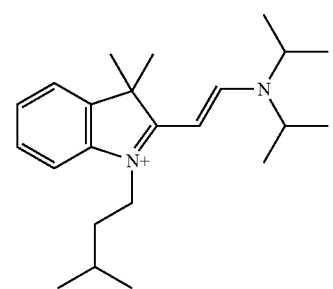
Compound No. 9
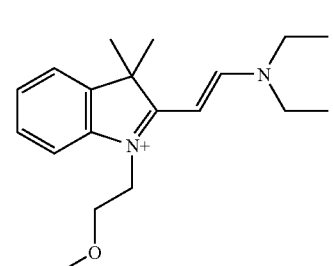
Compound No. 10
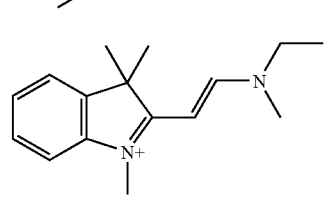
Compound No. 11
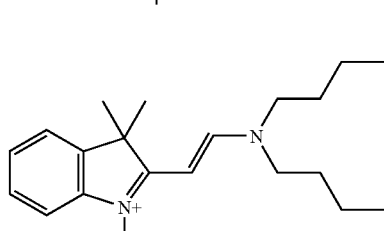
Compound No. 12
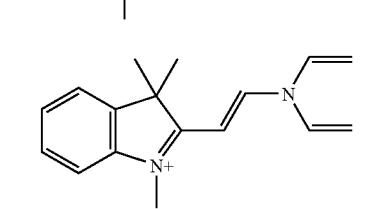
[Chemical Formula 7]
Compound No. 13
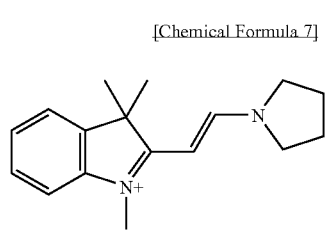
Compound No. 14
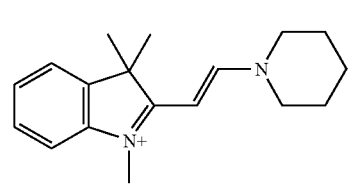
-continued
Compound No. 15
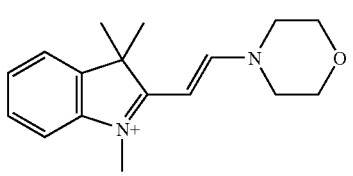
Compound No. 16
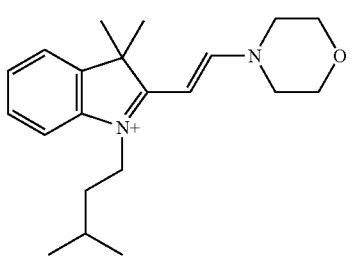
Compound No. 17
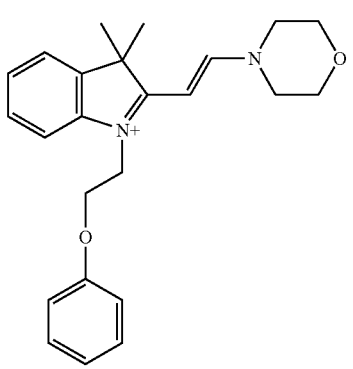
Compound No. 18
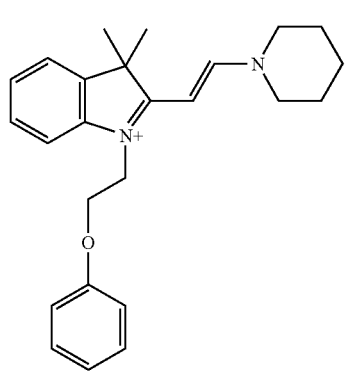
Compound No. 19
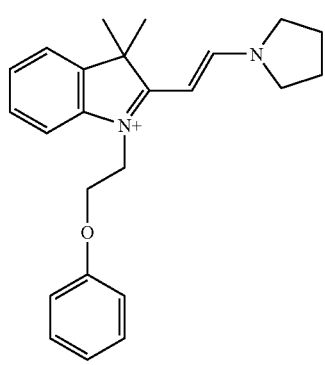

-continued
Compound No. 20
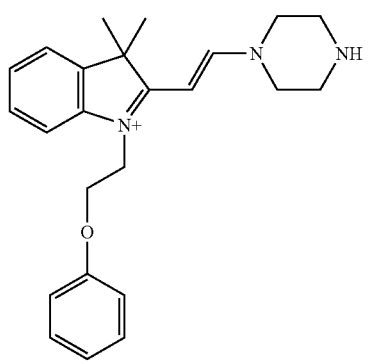
Compound No. 21
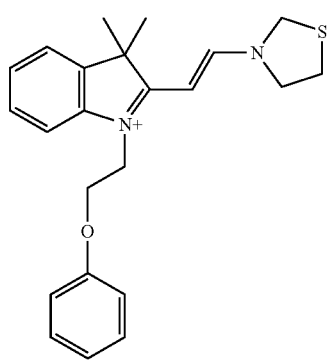
[Chemical Formula 8]
Compound No. 22
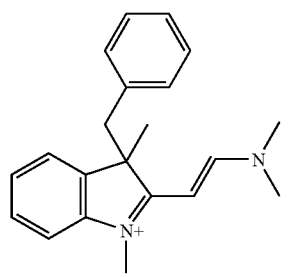
Compound No. 23
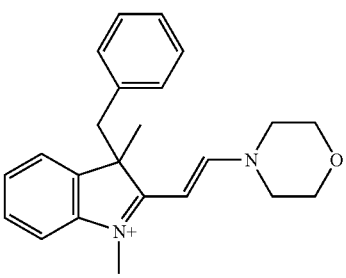
-continued
Compound No. 24
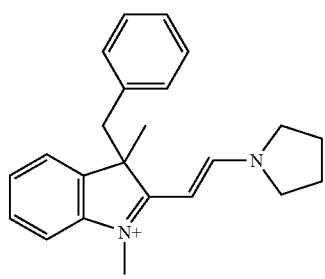
Compound No. 25
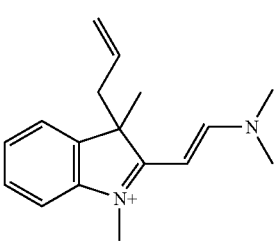
Compound No. 26
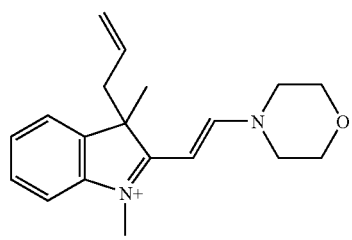
Compound No. 27
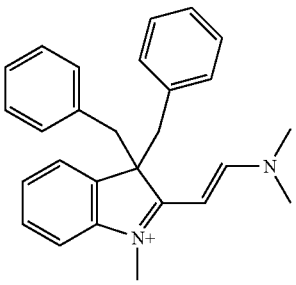
Compound No. 28
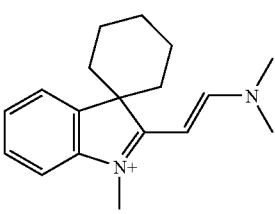

-continued
Compound No. 29
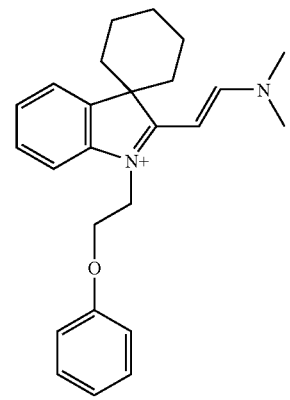
Compound No. 30
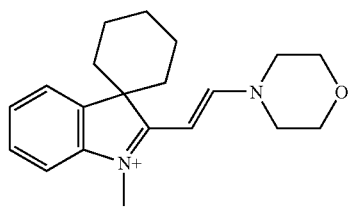
[Chemical Formula 9]
Compound No. 31
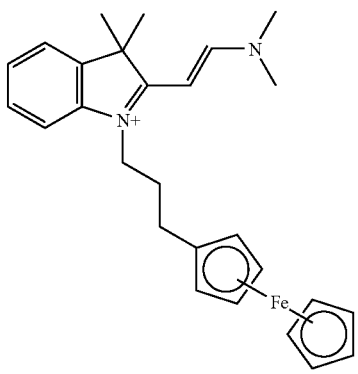
Compound No. 32
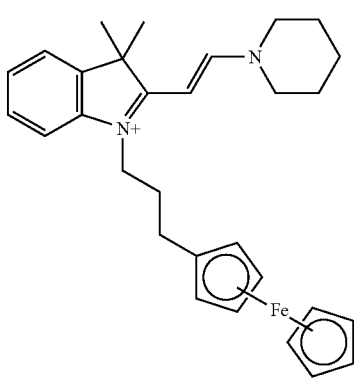
-continued
Compound No. 33
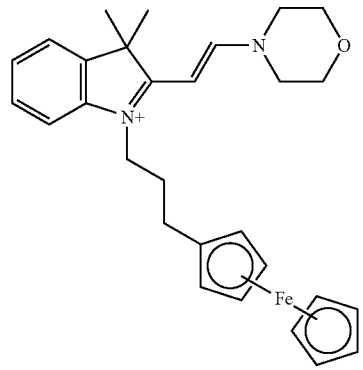
Compound No. 34
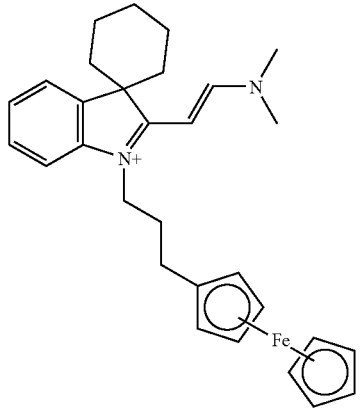
Compound No. 35
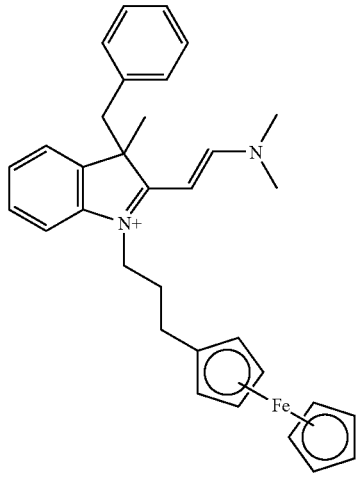

Compound No. 36
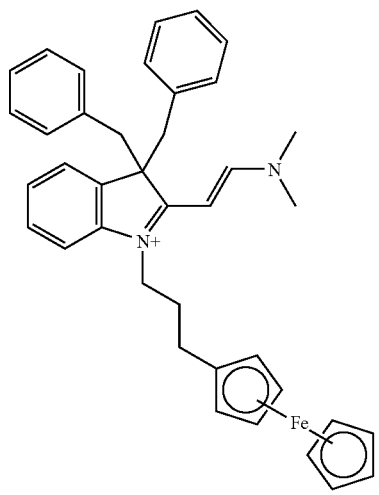
Compound No. 37
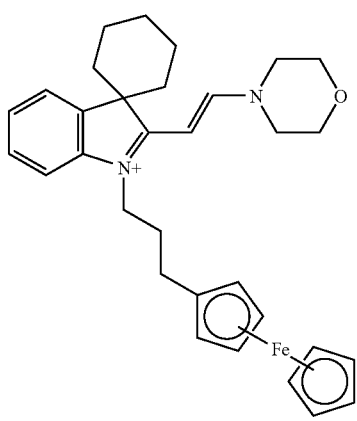
Compound No. 38
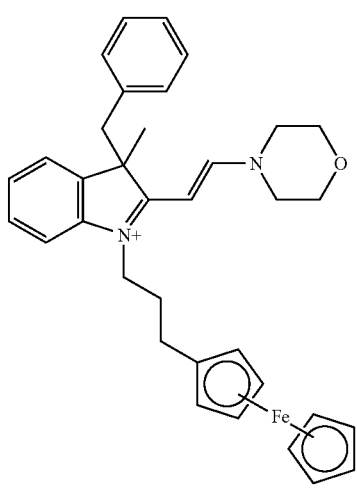
Compound No. 39
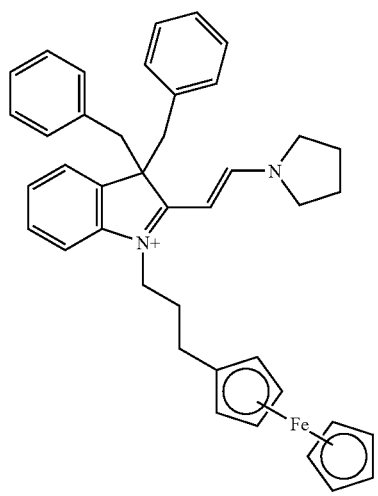
[Chemical Formula 10]
Compound No. 40
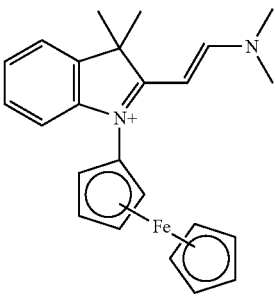
Compound No. 41
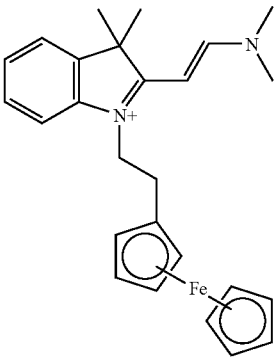

Compound No. 42
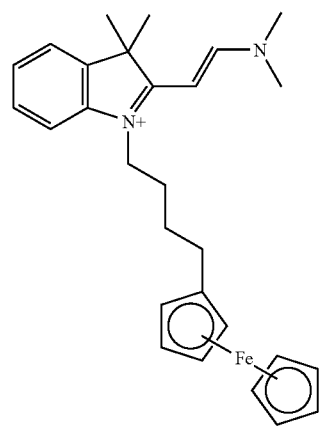
Compound No. 46
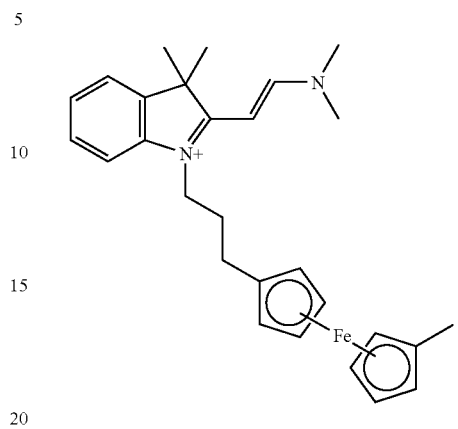
Compound No. 43
Compound No. 47
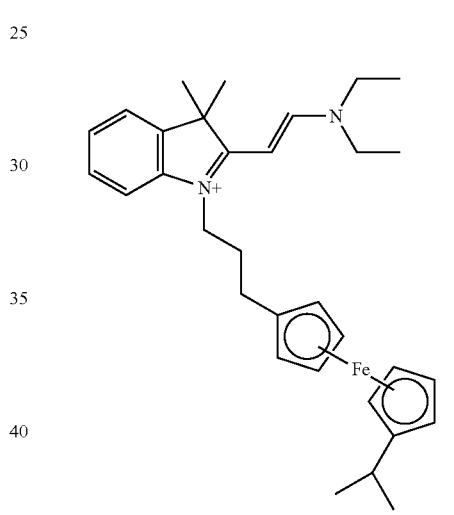
Compound No. 44
Compound No. 45
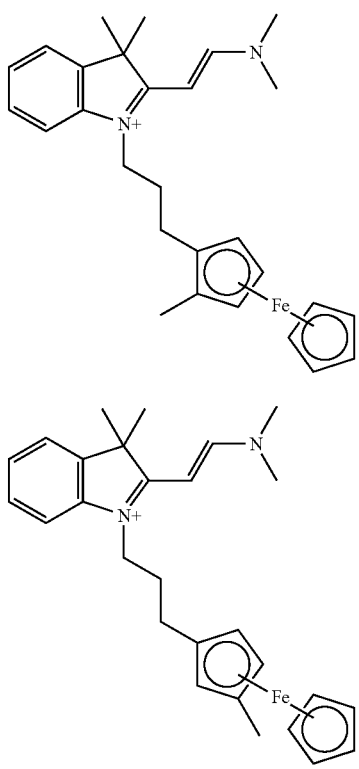
Compound No. 48
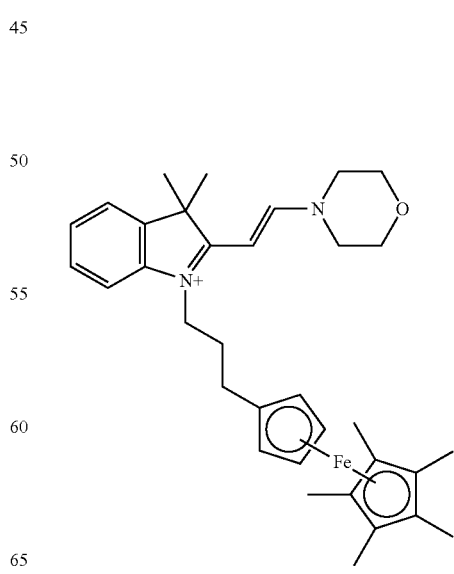

[Chemical Formula 11]
Compound No. 49
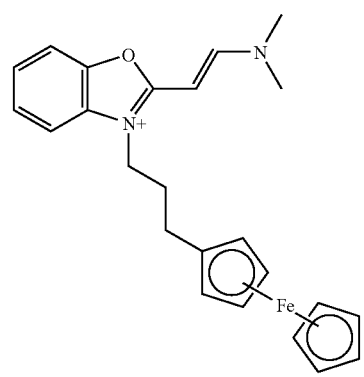
Compound No. 50
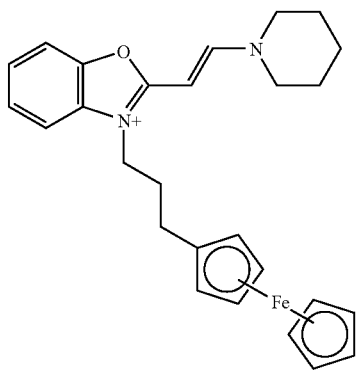
Compound No. 51
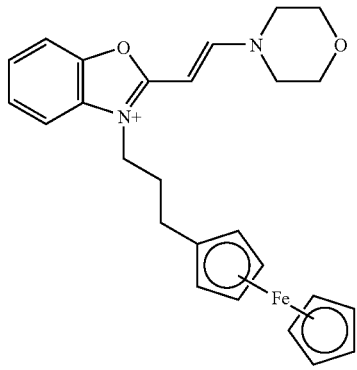
Compound No. 52
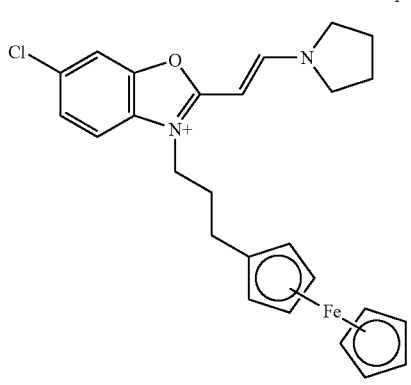
-continued
Compound No. 53
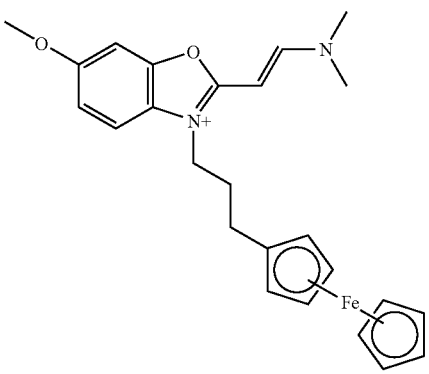
Compound No. 54
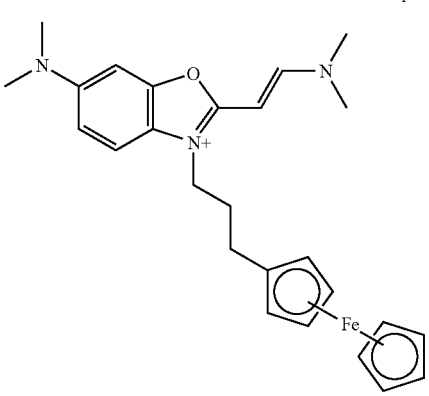
Compound No. 55
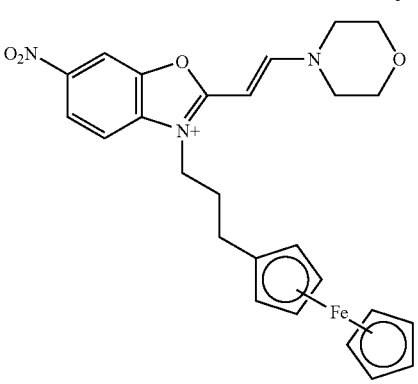
Compound No. 56
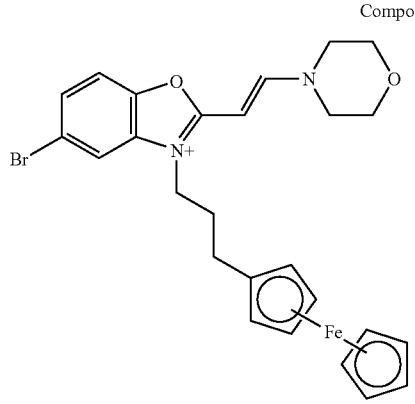

-continued

Compound No. 57

Compound No. 58
[Chemical Formula 12]

Compound No. 59

Compound No. 60

-continued

Compound No. 61

Compound No. 62

Compound No. 63

Compound No. 64

Compound No. 65

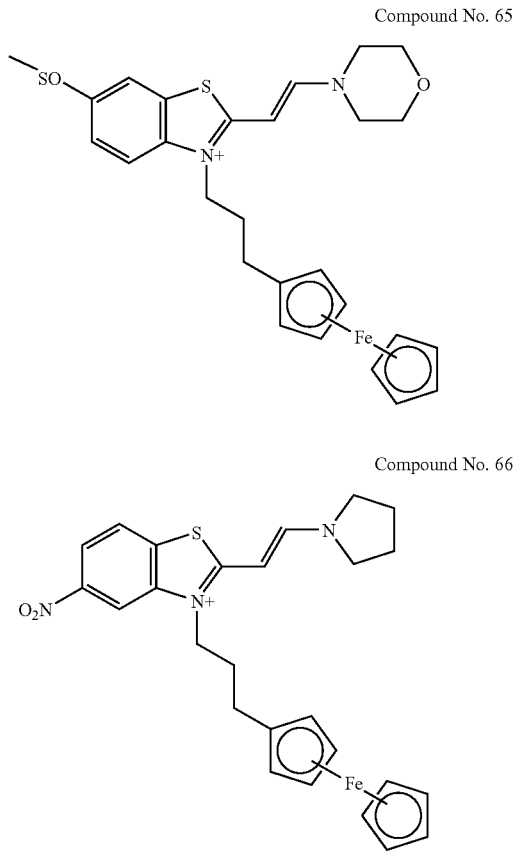

Compound No. 66

The method for producing the heterocyclic compound of the present invention represented by general formula (I) is not particularly limited. The compound can be obtained by a method in which publicly known reactions are utilized. For example, the heterocyclic compound represented by general formula (I') can be obtained by the synthetic route shown in [Chemical Formula 13] below, that is, by a reaction of a 2-methylheterocycle derivative and a formamide derivative using a reagent such as phosphorous oxychloride, followed by exchange of anions if necessary.

[Chemical Formula 13]

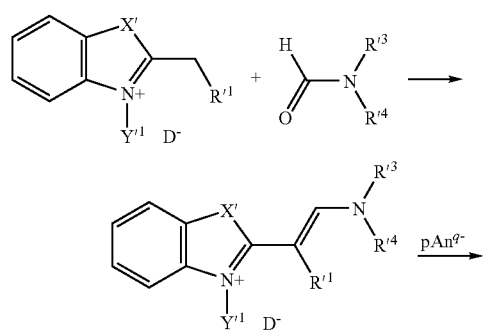

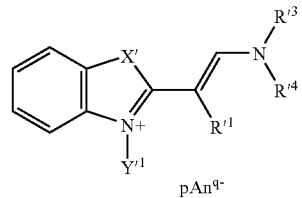

(In the formula, $R'^1$, $R'^3$, $R'^4$, $X'$, $Y'^1$, $An^{q-}$, and p are the same as those in general formula (I'), and $D^-$ represents an anion.)

$Y'^1$ in the above 2-methylheterocycle derivative can be introduced using $Y'^1$-D reactive to NH in the indole ring, wherein D represents a halogen atom such as chlorine, bromine, and iodine or a sulfonyloxy group such as phenylsulfonyloxy, 4-methylphenylsulfonyloxy, and 4-chlorophenylsulfoyloxy.

The above-mentioned heterocyclic compound of the present invention is suitable as an optical element for light in the wavelength range from 380 to 420 nm. The optical element means an element that functions upon absorbing light with specific characteristics, specifically including a light absorber, an optical recording substance, a photosensitizer, a UV absorber, and the like. For example, the optical recording substance is used for an optical recording layer in an optical recording medium such as an optical disc; the light absorber is used for an optical filter for an image displaying device such as a liquid crystal display (LCD), a plasma display panel (PDP), an electroluminescence display (ELD), a cathode-ray tube display (CRT), a fluorescent display tube, and an electric field emission display; and the UV absorber is used for imparting weather fastness to polymers, synthetic resins, coating materials, paint, or the like.

The heterocyclic compound of the present invention is particularly suitable as the optical recording substance used for an optical recording material owing to its optical properties. The optical recording material of the present invention is used for an optical recording layer in an optical recording medium wherein the optical recording layer is formed on a substrate. The optical recording material of the present invention comprises the heterocyclic compound of the present invention, including the heterocyclic compound of the present invention represented by general formula (I) itself and a mixture of the heterocyclic compound with an organic solvent described later and/or various kinds of compounds.

There is no particular limitation on the method for forming an optical recording layer in an optical recording medium using the optical recording material of the present invention. Generally, there may be used a wet coating method in which a substrate is coated by spin-coating, spraying, dipping, or the like with a solution prepared by dissolving the heterocyclic compound of the present invention in an organic solvent, which includes a lower alcohol such as methanol and ethanol; an ethereal alcohol such as methylcellosolve, ethylcellosolve, butylcellosolve, and butyldiglycol; a ketone such as acetone, methyl ethyl ketone, methyl isobutyl ketone, cyclohexanone, and diacetone alcohol; an ester such as ethyl acetate, butyl acetate, and methoxyethyl acetate; an acrylic ester such as ethyl acrylate and butyl acrylate; a fluoroalcohol such as 2,2,2-trifluoroethanol, perfluoroethanol, 2,2,3,3-tetrafluoro-1-propanol, and perfluoropropanol; a hydrocarbon such as benzene, toluene, and xylene; a chlorohydrocarbon such as dichloromethane, dichloroethane, and chloroform; and the like. Alternatively, there may be used a vapor deposition method, a sputtering method, or the like.

The thickness of the optical recording layer is typically 0.001 to 10μ, and preferably 0.01 to 5μ.

The heterocyclic compound of the present invention is preferably contained in the optical recording layer in the optical recording medium in an amount of 25 to 100% by mass. In order to form an optical recording layer with such a content of the heterocyclic compound, the optical recording material of the present invention preferably contains the heterocyclic compound of the present invention in an amount of 25 to 100% by mass with respect to the solid content of the optical recording material of the present invention.

In addition to the heterocyclic compound of the present invention represented by general formula (I), the optical recording layer optionally contains a compound used for optical recording layers such as a cyanine compound, an azo compound, an azomethine compound, a phthalocyanine compound, an oxonol compound, a squarylium compound, a styryl compound, a carbostyril compound, a naphthyridine compound, a porphyrin compound, a porphycene compound, an anthraquinone compound, a formazane metal complex, a pyrromethene metal complex, a fullerene dye; a resin such as polyethylene, polyester, polystyrene, and polycarbonate; a surfactant; an antistatic agent; a lubricant; a flame retardant; a radical scavenger such as a hindered amine; a pit-formation enhancer such as a ferrocene derivative; a dispersant; an antioxidant; a crosslinker; a photostabilizer; and the like. Furthermore, the optical recording layer may contain, as a quencher of singlet oxygen or the like, an aromatic nitroso compound, an aminium compound, an iminium compound, a bisiminium compound, a transition metal chelate compound, or the like. These compounds are preferably used in the optical recording layer in an amount of 0 to 75% by mass. In order to satisfy this condition, the content of these compounds in the optical recording material of the present invention is preferably 0 to 75% by mass with respect to the solid content of the optical recording material.

There is no particular limitation on the material for the substrate on which the above-described optical recording layer is laminated as long as the material is substantially transparent to the light for writing (recording) and the light for reading (playing-back). For example, there may be used a resin such as polymethylmethacrylate, polyethylene terephthalate, and polycarbonate, glass, or the like. The shape of the substrate may be arbitrarily selected according to the use, for example, tape, drum, belt, disc, and the like.

On the optical recording layer, there may be formed a reflective film by a vapor deposition method or a sputtering method using gold, silver, aluminum, copper, or the like; and there may be formed a protective layer using an acrylic resin, a UV-curable resin, or the like.

EXAMPLES

Hereinafter, the present invention will be described in further detail with respect to Examples. However, the present invention is not limited to the examples.

Example 1

Production of Heterocyclic Compounds

According to the following synthetic methods, hexafluorophosphate salt of each of compounds No. 1, 2, 6, 8, 15, 16, 17, 18, 19, 22, 23, and 31 was synthesized (Examples 1-1 to 1-12). The yields and results of analyses for the obtained compounds are shown in Tables 1 and 2. Each of the obtained compounds was confirmed to be the desired compound from the IR and $^1$H-NMR spectra shown in Tables 1 and 2.

In Table 1, the optical properties ($\lambda_{max}$ and $\epsilon$) are the values measured for a chloroform solution containing the compound in a concentration of $9.22 \times 10^{-6}$ mol/L, and the melting point is the temperature of the beginning of endothermic peak due to melting in the DTA curve obtained from differential scanning calorimetry at a temperature increasing rate of 10° C./min.

(Synthetic Method)

A reaction flask was charged with 30 ml of chloroform and 103 mmol of a formamide derivative, to which 15 mmol of phosphorus oxychloride was added at 4° C., and the mixture was stirred at 4° C. for 1 hr. To this mixture, 12.7 mmol of a 2-methylheterocycle derivative was added at 4° C. and the resultant mixture was heated to 70° C. and stirred for 2 hr. This reaction solution was poured into a solution prepared by dissolving 14.0 mmol of potassium hexafluorophosphate in 200 ml of water, and 200 ml of chloroform was added here. The resultant mixture was stirred well and the aqueous layer was discarded. The resultant organic layer was dried over anhydrous sodium sulfate and the solvent was removed to obtain residue. Toluene was added to the residue, and the resultant crude crystalline material was recrystallized using a mixed solvent of acetone and toluene to obtain the desired heterocyclic compound.

TABLE 1

|  | Heterocyclic cation | Yield (%) | $\lambda_{max}$ (nm) | $\epsilon$ (×10$^4$) | Melting point (° C.) | IR spectrum (cm$^{-1}$) |
|---|---|---|---|---|---|---|
| Example 1-1 | Compound No. 1 | 48 | 374 | 3.90 | 231 | 2986, 1634, 1567, 1490, 1406, 1281, 1235, 1120, 838, 808 |
| Example 1-2 | Compound No. 2 | 52 | 374 | 4.49 | 150 | 2958, 1640, 1570, 1417, 1267, 1195, 838, 799 |
| Example 1-3 | Compound No. 6 | 39 | 377 | 3.80 | 144 | 1632, 1557, 1487, 1413, 1269, 1249, 1195, 840, 754 |
| Example 1-4 | Compound No. 8 | 18 | 379 | 4.05 | 132 | 2978, 1620, 1605, 1548, 1460, 1313, 1298, 1201, 1140, 1101, 998, 841, 763 |
| Example 1-5 | Compound No. 15 | 52 | 379 | 4.21 | 171 | 2977, 1626, 1608, 1558, 1451, 1421, 1276, 1247, 1233, 1116, 1022, 841, 806, 762 |

TABLE 1-continued

|  | Heterocyclic cation | Yield (%) | $\lambda_{max}$ (nm) | $\epsilon$ (×10⁴) | Melting point (° C.) | IR spectrum (cm⁻¹) |
|---|---|---|---|---|---|---|
| Example 1-6 | Compound No. 16 | 77 | 379 | 4.45 | 227 | 2958, 1629, 1561, 1466, 1270, 1197, 1116, 1026, 836, 796 |
| Example 1-7 | Compound No. 17 | 46 | 381 | 4.28 | 171 | 2937, 1626, 1607, 1553, 1467, 1433, 1198, 1107, 1024, 841, 758 |
| Example 1-8 | Compound No. 18 | 26 | 379 | 4.51 | 146 | 2951, 1626, 1610, 1555, 1468, 1271, 1198, 840, 758 |
| Example 1-9 | Compound No. 19 | 46 | 380 | 3.96 | 126 | 2975, 1625, 1609, 1560, 1459, 1416, 1243, 1198, 1103, 841, 757, 693 |
| Example 1-10 | Compound No. 22 | 64 | 378 | 3.99 | 187 | 2942, 1637, 1567, 1482, 1408, 1277, 1258, 1233, 1125, 1105, 840, 771, 708 |
| Example 1-11 | Compound No. 23 | 77 | 383 | 4.27 | 186 | 2974, 1626, 1609, 1556, 1451, 1421, 1279, 1236, 1114, 1023, 841, 761, 706 |
| Example 1-12 | Compound No. 31 | 51 | 375 | 4.10 | 169 | 2932, 1632, 1560, 1469, 1414, 1275, 1191, 1120, 842 |

TABLE 2

|  | Heterocyclic cation | ¹H-NMR (Solvent: DMSO-d₆) |
|---|---|---|
| Example 1-1 | Compound No. 1 | 8.33(d, 1H, J=12.7Hz), 7.58(d, 1H, J=7.3Hz), 7.45-7.30(m, 2H), 7.23(dd, 1H, J=7.6, 6.8Hz), 5.60(d, 1H, J=12.7Hz), 3.56(s, 3H), 3.49(s, 3H), 3.23(s, 3H), 1.60(s, 6H) |
| Example 1-2 | Compound No. 2 | 8.35(d, 1H, J=12.4Hz), 7.59(d, 1H, J=7.3Hz), 7.40(dd, 1H, J=7.8, 7.6Hz), 7.33(d, 1H, J=7.8Hz), 7.24(dd, 1H, J=7.6, 7.3Hz), 5.56(d, 1H, J=12.4Hz), 4.10(t, 2H, J=7.6Hz), 3.49(s, 3H), 3.23(s, 3H), 1.78-1.62(m, 1H), 1.60(s, 6H), 1.58-1.45(m, 2H), 0.97(d, 6H, J=6.6Hz) |
| Example 1-3 | Compound No. 6 | 8.36(d, 1H, J=12.4Hz), 7.56(d, 1H, J=7.3Hz), 7.44(d, 1H, J=7.8Hz), 7.40(dd, 1H, J=7.8, 7.3Hz), 7.23(dd, 3H, J=8.3, 7.6Hz), 6.90(dd, 1H, J=7.3, 7.3Hz), 6.81(d, 2H, J=8.3Hz), 5.78(d, 1H, J=12.4Hz), 4.57(t, 2H, J=4.9Hz), 4.36(t, 2H, J=4.9Hz), 3.50(s, 3H), 3.19(s, 3H), 1.58(s, 6H) |
| Example 1-4 | Compound No. 8 | 8.34(d, 1H, J=12.9Hz), 7.62(d, 1H, J=7.3Hz), 7.42(dd, 1H, J=8.1, 7.1Hz), 7.36(d, 1H, J=7.3Hz), 7.27(dd, 1H, J=8.3, 7.3Hz), 5.88(d, 1H, J=12.7Hz), 4.55(dq, 1H, J=6.6, 6.6Hz), 4.20-4.09(m, 3H), 1.79-1.65(m, 1H), 1.61(s, 6H), 1.58-1.48(m, 2H), 1.36(d, 6H, J=6.8Hz), 1.32(d, 6H, J=6.6Hz), 0.97(d, 6H, J=6.6Hz) |
| Example 1-5 | Compound No. 15 | 8.32(d, 1H, J=12.7Hz), 7.59(d, 1H, J=7.3Hz), 7.45-7.31(m, 2H), 7.25(dd, 1H, J=7.3, 7.3Hz), 5.85(d, 1H, J=12.7Hz), 3.98-3.74(m, 2H), 3.89-3.83(m, 2H), 3.82-3.74(m, 4H), 3.58(s, 3H), 1.62(s, 6H) |
| Example 1-6 | Compound No. 16 | 8.34(d, 1H, J=12.7Hz), 7.60(d, 1H, J=7.3Hz), 7.41(dd, 1H, J=8.1, 7.3Hz), 7.32(d, 1H, J=7.8Hz), 7.25(dd, 1H, J=7.6, 6.8Hz), 5.82(d, 1H, J=12.7Hz), 4.12(t, 2H, J=7.6Hz), 4.00-3.90(m, 2H), 3.87-3.73(m, 6H), 1.78-1.65(m, 1H), 1.62(s, 6H), 1.56-1.48(m, 2H), 0.96(d, 6H, J=6.6Hz) |
| Example 1-7 | Compound No. 17 | 8.35(d, 1H, J=12.7Hz), 7.58(d, 1H, J=7.3Hz), 7.46(d, 1H, J=8.1Hz), 7.40(dd, 1H, J=8.1, 7.1Hz), 7.30-7.20(m, 3H), 6.91(dd, 1H, J=7.3, 7.3Hz), 6.80(d, 2H, J=8.5Hz), 6.00(d, 1H, J=12.7Hz), 4.58(t, 2H, J=4.8Hz), 4.34(t, 2H, J=4.9Hz), 4.00-3.90(m, 2H), 3.85-3.70(m, 6H), 1.60(s, 6H) |
| Example 1-8 | Compound No. 18 | 8.29(d, 1H, J=12.7Hz), 7.56(d, 1H, J=7.3Hz), 7.46-7.35(m, 2H), 7.30-7.18(m, 3H), 6.90(dd, 1H, J=7.3, 7.3Hz), 6.80(d, 2H, J=8.5Hz), 5.98(d, 1H, J=12.7Hz), 4.57(t, 2H, J=4.6Hz), 4.33(t, 2H, J=4.6Hz), 3.81(br, 2H), 3.73(br, 2H), 1.67(br, 6H), 1.58(s, 6H) |
| Example 1-9 | Compound No. 19 | 8.58(d, 1H, J=12.7Hz), 7.56(d, 1H, J=7.3Hz), 7.43(dd, 1H, J=7.8, 6.8Hz), 7.39(dd, 1H, J=8.1, 7.1Hz), 7.23(dd, 3H, J=7.8, 7.6Hz), 6.90(dd, 1H, J=8.1, 6.6Hz), 6.81(d, 2H, J=8.8Hz), 5.65(d, 1H, J=12.4Hz), 4.54(t, 2H, J=4.9Hz), 4.36(t, 2H, J=4.9Hz), 3.90(t, 2H, J=6.8Hz), 3.52(t, 2H, J=6.6Hz), 2.15-1.89(m, 4H), 1.58(s, 6H) |
| Example 1-10 | Compound No. 22 | 8.46(d, 1H, J=12.4Hz), 7.64(d, 1H, J=7.3Hz), 7.31(dd, 1H, J=7.6, 7.6Hz), 7.24(dd, 1H, J=7.6, 7.3Hz), 7.12(d, 1H, J=7.8Hz), 7.08-6.98(m, 3H), 6.63(d, 2H, J=7.1Hz), 5.61(d, 1H, J=12.7Hz), 3.54(s, 3H), 3.52(d, 1H, J=15.6Hz), 3.44(d, 1H, J=14.4Hz), 3.29(s, 3H), 3.27(s, 3H), 1.76(s, 3H) |
| Example 1-11 | Compound No. 23 | 8.42(d, 1H, J=12.7Hz), 7.64(d, 1H, J=7.3Hz), 7.33(dd, 1H, J=7.8, 7.6Hz), 7.26(dd, 1H, J=7.6, 7.3Hz), 7.15(d, 1H, J=7.8Hz), 7.10-6.99(m, 3H), 6.69(d, 2H, J=7.1Hz), 5.85(d, 1H, J=12.9Hz), 3.98(br, 2H), 3.93-3.75(m, 6H), 3.53(d, 1H, J=13.4Hz), 3.46(d, 1H, J=13.7Hz), 3.31(s, 3H), 1.78(s, 3H) |

TABLE 2-continued

| | Heterocyclic cation | $^1$H-NMR (Solvent: DMSO-$d_6$) |
|---|---|---|
| Example 1-12 | Compound No. 31 | 8.34(d, 1H, J=12.4Hz), 7.59(d, 1H, J=7.6Hz), 7.48-7.40(m, 2H), 7.24(dd, 1H, J=7.3, 7.1Hz), 5.55(d, 1H, J=12.8Hz), 4.19-4.05(m, 11H), 3.48(s, 3H), 3.19(s, 3H), 2.41(dd, 2H, J=8.1, 7.3Hz), 1.92(ddt, 2H, J=8.1, 8.1, 6.8Hz), 1.61(s, 6H) |

Example 2

Evaluation of Heterocyclic Compounds 1

An optical recording layer was formed on a polycarbonate disc substrate having a diameter of 12 cm by spin coating (2000 rpm, 60 sec) with a 2,2,3,3-tetrafluoropropanol solution containing 1.0% by mass of each heterocyclic compound obtained in Example 1 (see Table 3) to prepare an optical recording medium (Examples 2-1 to 2-6). The UV spectra were measured in transmission mode and in reflection mode with an incident angle of 5° for each of these optical recording media. The results are shown in Table 3.

The spectrum in reflection mode of an optical recording medium is related to playing-back characteristics thereof. In the playing-back mode, presence or absence of recording is detected based on the difference in the amount of light at the wavelength of laser for the laser light reflected on the optical recording medium. Accordingly, more preferred is an optical recording medium having the absorption maximum measured in reflection mode closer to the wavelength of the light used for playing back.

TABLE 3

| No. | Heterocyclic compound | $\lambda_{max}$ (nm) in transmission mode | $\lambda_{max}$ (nm) in reflection mode |
|---|---|---|---|
| Example 2-1 | PF$_6^-$ salt of Compound No. 1 | 370 | 407 |
| Example 2-2 | PF$_6^-$ salt of Compound No. 6 | 373 | 405 |
| Example 2-3 | PF$_6^-$ salt of Compound No. 15 | 373 | 409 |
| Example 2-4 | PF$_6^-$ salt of Compound No. 18 | 374 | 411 |
| Example 2-5 | PF$_6^-$ salt of Compound No. 22 | 375 | 413 |
| Example 2-6 | PF$_6^-$ salt of Compound No. 31 | 373 | 405 |

From Table 3, it was confirmed that the optical recording medium comprising the heterocyclic compound of the present invention is suitable for laser light at 405 nm.

Example 3

Evaluation of Heterocyclic Compounds 2

The optical recording medium obtained by the same procedures as those in Example 2 using the heterocyclic compound shown in Table 4 was irradiated with light with 55,000 lux for 48 hr. The residual percentages of absorbance at $\lambda_{max}$ after irradiation are shown in Table 4.

TABLE 4

| No. | Heterocyclic compound | Residual percentage (%) |
|---|---|---|
| Example 3-1 | PF$_6^-$ salt of Compound No. 1 | 14.5 |
| Example 3-2 | PF$_6^-$ salt of Compound No. 6 | 16.6 |
| Example 3-3 | PF$_6^-$ salt of Compound No. 17 | 13.4 |
| Example 3-4 | PF$_6^-$ salt of Compound No. 31 | 90.4 |

From Table 4, it was confirmed that the compound having a ferrocene-derived group at the side chain of N atom (Example 3-4) has especially excellent photostability among the heterocyclic compounds of the present invention.

INDUSTRIAL APPLICABILITY

The present invention can provide a compound suitable for an optical recording medium to which short-wavelength light is applied for recording and playing-back and an optical recording material comprising the compound.

The invention claimed is:

1. A heterocyclic compound represented by general formula (I):

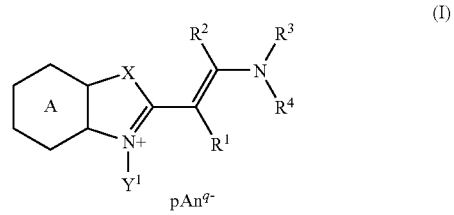

wherein
ring A represents a benzene ring optionally substituted with an alkyl group having 1 to 8 carbon atoms, a haloalkyl group having 1 to 8 carbon atoms, an alkoxy group having 1 to 8 carbon atoms, a haloalkoxy group having 1 to 8 carbon atoms, a cyano group, a nitro group, a sulfonyl group containing a hydrocarbon group having 1 to 12 carbon atoms, a sulfinyl group containing a hydrocarbon group having 1 to 12 carbon atoms, an alkylamino group wherein the alkyl has 1 to 8 carbon atoms, a dialkylamino group wherein each alkyl has 1 to 8 carbon atoms, an amido group having 1 to 8 carbon atoms, or a halogen atom; or a naphthalene ring optionally substituted with an alkyl group having 1 to 8 carbon atoms, a haloalkyl group having 1 to 8 carbon atoms, an alkoxy group having 1 to 8 carbon atoms, a haloalkoxy group having 1 to 8 carbon atoms, a cyano group, a nitro group, a sulfonyl group containing a hydrocarbon group having 1 to 12 carbon atoms, a sulfinyl group containing a hydrocarbon group having 1 to 12 carbon atoms, an alkylamino group wherein the alkyl has 1 to 8 carbon atoms, a dialkylamino group wherein each alkyl has 1 to 8 carbon atoms, an amido group having 1 to 8 carbon atoms, or a halogen atom;

X represents CR$^a$R$^b$ wherein R$^a$ and R$^b$ each represent a hydrocarbon group having 1 to 12 carbon atoms, which may be united to form a 3- to 6-membered ring;

R$^1$ and R$^2$ each represent independently a hydrogen atom, a halogen atom, a cyano group, an alkyl group having 1 to 4 carbon atoms, or an aralkyl group having 7 to 18 carbon atoms;

R³ and R⁴ each represent independently a hydrocarbon group having 1 to 4 carbon atoms or are united to form a heterocycle free from multiple bonds;

$An^{q-}$ represents a q-valent anion; q represents 1 or 2; and p represents a coefficient for satisfying the electric charge neutrality; and Y¹ represents a group represented by general formula (II):

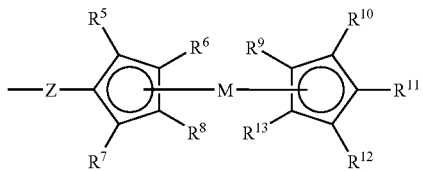

(II)

wherein R⁵ to R¹³ each represent independently a hydrogen atom, an optionally halogenated alkyl group having 1 to 4 carbon atoms in which (a) methylene group(s) in the chain is (are) optionally replaced by —O— or —CO—; M represents Fe, Co, Ni, Ti, Cu, Zn, Zr, Cr, Mo, Os, Mn, Ru, Sn, Pd, Rh, or Pt; and Z represents a direct bond or an alkylene group having 1 to 8 carbon atoms in which (a) methylene group(s) is (are) optionally replaced by —O—, —S—, —CO—, —COO—, —OCO—, —SO₂—, —NH—, —CONH—, —NHCO—, —N=CH—, or —CH=CH—.

2. A heterocyclic compound represented by general formula (I'):

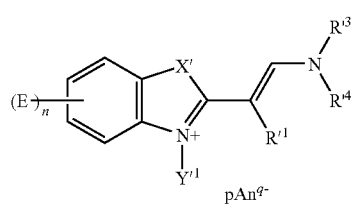

(I')

wherein
E represents an alkyl group having 1 to 8 carbon atoms, a haloalkyl group having 1 to 8 carbon atoms, an alkoxy group having 1 to 8 carbon atoms, a haloalkoxy group having 1 to 8 carbon atoms, a cyano group, a nitro group, a sulfonyl group containing a hydrocarbon group having 1 to 12 carbon atoms, a sulfinyl group containing a hydrocarbon group having 1 to 12 carbon atoms, an alkylamino group wherein the alkyl has 1 to 8 carbon atoms, a dialkylamino group wherein each alkyl has 1 to 8 carbon atoms, an amido group having 1 to 8 carbon atoms, or a halogen atom;

X' represents $CR'^{a}R'^{b}$ wherein $R'^{a}$ and $R'^{b}$ each represent a hydrocarbon group having 1 to 12 carbon atoms, which may be united to form a 3- to 6-membered ring;

R'¹ represents a hydrogen atom, a halogen atom, a cyano group, an alkyl group having 1 to 4 carbon atoms, or an aralkyl group having 7 to 18 carbon atoms;

R'³ and R'⁴ each represent independently a hydrocarbon group having 1 to 4 carbon atoms or are bonded to form a heterocycle free from multiple bonds;

n represents an integer of 0 to 4;

$An^{q-}$ represents a q-valent anion; q represents 1 or 2; and p represents a coefficient for satisfying the electric charge neutrality; and Y'¹ represents a group represented by general formula (II'):

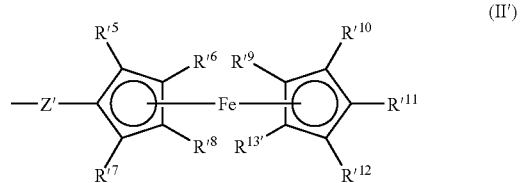

(II')

wherein R'⁵ to R'¹³ each represent independently a hydrogen atom or an optionally halogenated alkyl group having 1 to 4 carbon atoms in which (a) methylene group(s) in the chain is (are) optionally replaced by —O— or —CO—; and Z' represents a direct bond or an alkylene group having 1 to 8 carbon atoms.

3. The heterocyclic compound according to claim 2, wherein the group represented by Y'¹ in general formula (I') is the group represented by general formula (II').

4. An optical recording material comprising the heterocyclic compound according to claim 1, which is used for an optical recording layer of an optical recording medium, wherein the optical recording layer is formed on a substrate.

5. An optical recording material comprising the heterocyclic compound according to claim 2, which is used for an optical recording layer of an optical recording medium, wherein the optical recording layer is formed on a substrate.

6. An optical recording material comprising the heterocyclic compound according to claim 3, which is used for an optical recording layer of an optical recording medium, wherein the optical recording layer is formed on a substrate.

* * * * *